United States Patent
Christensen

(10) Patent No.: US 8,257,751 B2
(45) Date of Patent: Sep. 4, 2012

(54) COMPOSITION FOR THE COSMETIC TREATMENT OF AGE-RELATED DERMATOLOGICAL SYMPTOMS

(75) Inventor: Flemming Kjærgaard Christensen, Hadsund (DK)

(73) Assignee: Beauté Pacifique ApS, Hadsund (DK)

( * ) Notice: Subject to any disclaimer, the term of this patent is extended or adjusted under 35 U.S.C. 154(b) by 0 days.

(21) Appl. No.: 10/577,976

(22) PCT Filed: Nov. 3, 2004

(86) PCT No.: PCT/DK2004/000759
§ 371 (c)(1),
(2), (4) Date: Apr. 2, 2007

(87) PCT Pub. No.: WO2005/041854
PCT Pub. Date: May 12, 2005

(65) Prior Publication Data
US 2007/0292527 A1    Dec. 20, 2007

(30) Foreign Application Priority Data

Nov. 3, 2003    (DK) ................................ 2003 01631

(51) Int. Cl.
*A61K 36/00* (2006.01)
(52) U.S. Cl. ........................................................ 424/725
(58) Field of Classification Search .................. None
See application file for complete search history.

(56) References Cited

U.S. PATENT DOCUMENTS

| 6,028,118 A | * | 2/2000 | Dupont et al. | 424/548 |
| 6,149,939 A | * | 11/2000 | Strumor et al. | 424/464 |
| 2005/0113293 A1 | * | 5/2005 | Larsen et al. | 514/9 |

FOREIGN PATENT DOCUMENTS

| CA | 2358158 A1 | * | 4/2003 |
| DE | 10315025 A | * | 10/2004 |
| JP | 58079912 A | * | 5/1983 |
| JP | 09/05034223 | | 1/1993 |
| JP | 05246866 A | * | 9/1993 |
| JP | 06128121 A | * | 5/1994 |
| JP | 06279255 A | * | 10/1994 |
| JP | 07039339 A | * | 2/1995 |
| JP | 08310939 A | * | 11/1996 |
| JP | 09191852 A | * | 7/1997 |
| JP | 12/10100129 | | 2/1998 |
| JP | 11279069 A | * | 10/1999 |
| JP | 2001114634 A | * | 4/2001 |
| JP | 2001302525 A | * | 10/2001 |
| JP | 2003055190 A | * | 2/2003 |
| JP | 2003055246 A | * | 2/2003 |
| KR | 2001/000429 | | 1/2001 |
| KR | 2003/025895 | | 3/2003 |
| KR | 2003/057866 | | 7/2003 |
| WO | WO 01/85182 | | 11/2001 |

OTHER PUBLICATIONS

Saini, H.;Kamal, R.; and Sharma, A.; *Web Based Fuzzy Expert System for Integrated Pest Management in Soybean*; International Journal of Information Technology; Aug. 2002; vol. 8, No. 1; pp. 55-74.

* cited by examiner

*Primary Examiner* — Qiuwen Mi
(74) *Attorney, Agent, or Firm* — James Creighton Wray

(57) ABSTRACT

A composition comprising an extract of a deep sea fish; and an extract of rooibos aspalathus linearis); and optionally an extract of bearberry (arctostaphylos uva-ursi) as active components thereof; and optionally one or more fillers or ancillary agents conventionally used in the formulation of compositions is provided. Upon administration, the composition has beneficial effect in relation to the cosmetic treatment of age-related dermatological symptoms, such as wrinkled and/or aged skin as well as hair loss.

22 Claims, No Drawings

COMPOSITION FOR THE COSMETIC TREATMENT OF AGE-RELATED DERMATOLOGICAL SYMPTOMS

This application claims the benefit of Danish Application No. PA 2003 01631 filed Nov. 3, 2003 and PCT/DK2004/000759filed Nov. 3, 2004, which are hereby incorporated by reference in their entirety.

The present invention relates to a composition comprising an extract of a deep sea fish and an extract of rooibos and optionally an extract of bearberry as active ingredients. Furthermore, the present invention relates to methods of uses of such compositions in relation to dermatological conditions.

The composition according to the invention has been found to be effective for promoting collagen synthesis in the skin, and it is accordingly useful for cosmetic treatment of age-related dermatological symptoms, such as cosmetic treatment of wrinkled and/or aged skin and for cosmetic treatment of hair loss

BACKGROUND OF THE INVENTION

Usually, the compositions for cosmetic treatment of age-related dermatological symptoms, such as wrinkled skin, comprise lotions which according to the instructions of the products are to be applied onto the skin, for example the skin of the face or onto other parts of the body, where the expected effect is desired.

However, also compositions for cosmetic uses in the form of oral formulations have been described.

WO 01/85182 relates to a composition for oral administration comprising a cartilage extract and a plant extract comprising a hydrophilic antioxidant (e.g. grape seed extract) and a hydrophobic antioxidant (e.g. tomato extract). The composition is used for reducing signs of ageing of the skin. In WO 01/85182, it is stated that a combination of the cartilage extract and the grape seed extract and the tomato extract gives a symbiotic effect, compared to the combination of grape seed and tomato extract on the one hand (negative effect) and fish extract alone (positive effect) on the other hand (cf. page 7, lines 21-26). The disclosure of WO 01/85182 does not mention that the composition is effective against hair loss.

It is an object according to the present invention to provide an alternative composition which is effective for use in a cosmetic treatment of age-related dermatological symptoms, such as wrinkled and/or aged skin as well as hair loss.

BRIEF DESCRIPTION OF THE INVENTION

The object of the invention is in a first aspect solved by a composition comprising the components:
an extract of a deep sea fish; and
an extract of rooibos (aspalathus linearis); and
optionally an extract of bearberry (arctostaphylos uva-ursi);
as active components thereof; and
optionally one or more fillers or ancillary agents conventionally used in the formulation of compositions.

Another aspect according to the present invention is the provision of a method for the preparation of a composition according to the present invention, wherein the active components are mixed and via the conventional fillers or ancillary agents, if present, are formulated into the form suitable for the administration desired.

A further aspect according to the present invention is the provision of a method for the cosmetic treatment of age-related dermatological symptoms by administering an effective amount of a composition according to the present invention to a subject in need thereof.

A still further aspect according to the present invention is the provision of a composition according to the present invention for use as a medicament Yet a still further aspect according to the present invention is the use of a composition according to the present invention for the preparation of a medicament for the treatment of dermatological conditions.

DETAILED DESCRIPTION OF THE INVENTION

In the present description and the appended claims the expression "age-related dermatological symptoms" is to be interpreted as comprising those dermatological symptoms and/or indications which usually appear as a consequence of ageing, such as wrinkled and/or aged skin as well as hair loss. However, the expression is not limited to the above symptoms appearing in relation to an actual ageing process. Rather, the expression also comprises the above symptoms which may appear in subjects encountering the above symptoms of other reasons and/or of other origins, such as e.g. due to pathological conditions or the like.

According to one aspect according to the invention, a composition comprising the components:
an extract of a deep sea fish; and
an extract of rooibos (aspalathus linearis); and
optionally an extract of bearberry (arctostaphylos uva-ursi);
as active components thereof; and
optionally one or more fillers or ancillary agents conventionally used in the formulation of compositions,
is provided.

The extract of the deep sea fish, which is employed according to the present invention, may originate from a range of different sources, i.e. fish species. However, it has been found convenient to employ extracts of shark fish due to the wide abundance of such material on the commercial market. Such material is available e.g. as powders. Preferably the extract of deep sea fish is obtained as powder from the company Real Life, Fort Collins, Colo. USA. It is preferred in the composition according to the present invention to use extracts of shark fish having a protein content of 15-70 wt %, for example 20-60 wt %, such as 30-50 wt %, preferably 35-45 wt %.

The daily dosage of the extract of the deep sea fish to be administered is conveniently from 100 to 1600 mg, such as 200 to 1200 mg, e.g. 300 to 1000 mg, preferably 400 to 900 mg, such as 600 to 800 mg.

The above ranges are suitable for oral administration. However, for topical administration, an appropriate daily dosage of the extract of the deep sea fish will usually be obtained if a lotion to be administered two times pr. day comprises 0.25-2.0, such as 0.5-1.5, for example 1.0 wt % of the extract of a deep sea fish.

The extract of rooibos (aspalathus linearis) originates from the South African plant Aspalathus Linearis and has been known and used by tribes of South Africa for ages. In the later years, the use of rooibos has spread to most part of the western world, and its use as tea is now very popular. In the composition according to the present invention, the rooibos is preferably used as the powder Herbasec MPE Rooibos or as the liquid Herbasol MPE Rooibos, both commercially available from Cosmochem International Ltd., Steinhausen, Switzerland.

The daily dosage of the extract of the rooibos (aspalathus linearis) to be administered is conveniently from 5 to 40 mg, such as 8 to 35 mg, e.g. 10 to 30 mg, preferably 15 to 25 mg, such as 18 to 23 mg.

The above ranges are suitable for oral administration. However, for topical administration, an appropriate daily dosage of the extract of the rooibos (aspalathus linearis) will usually be obtained if a lotion to be administered two times pr. day comprises 2-20, such as 1-15, for example 2-12, e.g. 3-10, such as 5-8 wt % of the Rooibos extract.

The extract of bearberry is obtained from the plant arctostaphylos uva-ursi. Such extracts has long been known and utilised as an anti-bacterial and antiseptic agent Furthermore, the plant material has also been shown to be useful for treatment of a range of renal diseases. The plant material is commercially available in the form of crushed or powdered leaves. In the composition according to the present invention, the bearberry extract is preferably used as the product Melfade or Melfade-J, both commercially available from Pentapharm, Basel, Switzerland.

The daily dosage of the extract of the bearberry (arctostaphylos uva-ursi) to be administered is conveniently from 5 to 40 mg, such as 8 to 35 mg, e.g. 10 to 25 mg, preferably 12 to 20 mg, such as 14 to 18 mg.

The administration of the composition according to the present invention may take place in one daily dose or in divided administration 1, 2, 3 or 4 times per day.

In one embodiment of the composition according to the present invention, the composition does not comprise the extract of bearberry (arctostaphylos uva-ursi).

Such an embodiment is preferably formulated as a tablet further comprising suitable ancillary agents and fillers as well as coating agents.

In another embodiment of the composition according to the present invention, the composition comprises an extract of deep sea fish and an extract of rooibos (aspalathus linearis) as well as an extract of bearberry (arctostaphylos uva-ursi).

Such an embodiment is preferably formulated as a tablet further comprising suitable ancillary agents and fillers as well as coating agents.

In a still further embodiment of the composition according to the present invention, the composition additionally comprises one or two components selected from the group comprising horsetail extract (equisetum arvense L.) and a shellfish extract.

Horsetail (equisetum arvense L.) is commercially available as a powder extract from most herb suppliers.

The horsetail extract (equisetum arvense L.) is, if present, preferably included in an amount corresponding to a daily dose of 20-140, such as 40-120, for example 60-100, such as 80 mg.

Shellfish extract is available among others from Qingdao Jinronga International Trading Co., Ltd, China. Preferably an amount of the shell fish extract corresponding to a daily intake of less than 500 mg is included in the composition according to the present invention.

Such additionally components have been found to further improve the effect of the composition according to the present invention.

Additionally, in a preferred embodiment of the composition according to the present invention, diacetyl boldine may also be included in the composition. Preferably, diacetyl boldine is, if included, the product Lumiskin, commercially available from Sederma, France.

Furthermore, the composition according to the present invention may additionally comprise one or more components selected from the group comprising: Vitamin A, Vitamin C, zinc, D-alpha-tocopherol, betaine, diazolidenyl urea, citric acid, sodium ascorbylic phosphate, alpha-lipoic acid and methylsulfonyl methane.

Such addition agents have been shown to have a positive impact on the effects obtained.

In one aspect according to the present invention, a method for the cosmetic treatment of age-related dermatological symptoms by administering an effective amount of the composition according to the present invention to a subject in need thereof is provided.

In a preferred embodiment, the invention relates to the cosmetic treatment of wrinkled and/or aged skin.

In another preferred embodiment, the invention relates to the cosmetic treatment of hair loss.

The composition according to the present invention is preferably administered by oral and/or topical routes.

In case of treatment of wrinkled and/or aged skin, the composition is preferably administered by the oral route; and in case of treatment of hair loss, the composition may be administered by an oral route or administered by application of a topical formulation comprising the composition onto the scalp.

In one aspect, the present invention relates to a method for the preparation of a composition according to any of the preceding claims, wherein the active components are mixed and via the conventional fillers or ancillary agents, if present, are formulated into the form of administration desired.

In another aspect of the present invention, the composition of the present invention is in a form suitable for oral administration.

For administration by an oral route, the composition is preferably formulated as a tablet, a capsule, a lozenge or a sachet.

A composition according to the present invention intended for oral formulation may contain one or more fillers or ancillary agents conventionally used in oral formulations. These additional agents may comprise lactose, cellulose, glucose, saccharose, starch, talc, magnesium stearate, silicon dioxide, magnesium carbonate, and coating agents etc.

In another aspect of the present invention, the composition of the present invention is in a form suitable for topical administration onto the scalp.

For topical administration, the formulation according to the present invention is preferably in the form of a lotion, a cream, an emulsion, a foundation, a shampoo, a rinse, a hair liquid, a set lotion or a hair tonic.

A composition according to the present invention intended for topical formulation may contain one or more ancillary agents conventionally used in topical formulations. These additionally agents may be solvents, binders, vehicles, preservatives, complexing agents and pH regulators etc.

Such liquid formulations may be obtained by dispersing the active components and optionally further adding one or more ancillary agents conventionally used in topical formulations.

Preferred embodiments of the composition of the invention may, furthermore, comprise a range of generally accepted ingredients, such as vitamins and nutritional agents and herbals as listed in "Martindale—The Complete Drug Reference", edition 2002.

The above formulations may be prepared in a manner known per se, and a person skilled in the art will know how to make such formulations. For a more detailed description, reference is made to: Remington's Pharmaceutical Sciences, Mack Publishing Company, Pa. USA, 15$^{th}$ Edition.

The composition according to the present invention is preferably formulated so as to be administered 1-4 times per day, such as 2 to 3 times per day. Preferably, the composition according to the present invention is administered two times per day, such as in the morning and in the evening.

Further aspects according to the present invention relates to the use of a composition according to the invention for use as a medicament and/or for the preparation of a medicament for the treatment of dermatological conditions.

Examples of such conditions in which the composition according to the present invention may be useful are: chaped skin, cracks, fissures, dermatitis, reconstitution of scar tissue, healing of skin wounds and reconstitution of skin after treatment with corticosteroids, alopecia areata and various alopecias, actinic keratoses, photo damage, eczemas, psoriasis and various hyperkeratoses.

Such medicaments may be used for curative as well as (where applicable) prophylactic treatment.

EXAMPLES

Example 1

Manufacture of tablets comprising extract of shark fish, extract of rooibos (aspalathus linearis) and extract of bearberry (arctostaphylos uva-ursi).

800.0 g extract of shark fish and 22.0 g extract of rooibos (aspalathus linearis) and 16.0 g extract of bearberry (arctostaphylos uva-ursi) are thoroughly mixed with 210.0 g microcrystalline cellulose and 14.0 g silicon dioxide (2.4 to 3.6 micron). The mixture is compressed into tablets having a weight of approximately 531 mg each.

Example 2

Manufacture of capsules comprising extract of shark fish and extract of rooibos (aspalathus linearis)

900.0 g extract of shark fish and 30.0 g extract of rooibos (aspalathus linearis are thoroughly mixed. The mixture is filled in gelatine capsules (465.0 mg in each), giving 2000 capsules each containing: 450 mg extract of shark fish and 15 mg extract of rooibos (aspalathus linearis).

Example 3

Manufacture of tablets comprising extract of shark fish, extract of rooibos (aspalathus linearis). 800.0 g extract of shark fish and 22.0 g extract of rooibos (aspalathus linearis) are thoroughly mixed with 210.0 g microcrystalline cellulose and 14.0 g silicon dioxide (2.4 to 3.6 micron). The mixture is compressed into tablets with a weight of (523 mg each). Each tablet contains approximately 400 mg extract of shark fish and 11 mg extract of rooibos (aspalathus linearis).

Example 4

Manufacture of a lotion comprising extract of shark fish and extract of rooibos (aspalathus linearis)

A lotion having the following composition is manufactured.

TABLE 1

| Component No. | Component | Amount (wt %) |
| --- | --- | --- |
| 1 | 96% ethyl alcohol | 10 |
| 2 | glycerol | 5 |
| 3 | Polyoxyethylene (EO = 20) stearate | 0.5 |
| 4 | extract of shark fish | 1 |

TABLE 1-continued

| Component No. | Component | Amount (wt %) |
| --- | --- | --- |
| 5 | extract of rooibos | 10 |
| 6 | Dimethylaminopropyl lanolin acid amide disulphate | 0.04 |
| 7 | Methyl paraben | 0.2 |
| 8 | Water | to 100 wt % |

Mixture 1: A mixture is prepared by thoroughly mixing component 6 and component 2, followed by addition of component 8 during stirring.

Mixture 2: Another mixture is prepared by admixing component 7, component 3 and component 4 and 5 in component 1.

Mixture 1 is added to mixture 2 during stirring to obtain a lotion according to the present invention.

Example 5

Manufacture of a lotion comprising extract of shark fish and extract of rooibos (aspalathus linearis)

A lotion having the following composition is manufactured:

TABLE 2

| Component No. | Component | Amount (wt %) |
| --- | --- | --- |
| 1 | 96% ethyl alcohol | 5 |
| 2 | glycerol | 5 |
| 3 | Polyoxyethylene (EO = 20) stearate | 0.5 |
| 4 | extract of shark fish | 1 |
| 5 | extract of rooibos | 10 |
| 6 | Extract of shell fish | 1 |
| 7 | Dimethylaminopropyl lanolin acid amide disulphate | 0.04 |
| 8 | Methyl paraben | 0.2 |
| 9 | Water | to 100 wt % |

Mixture 1: A mixture is prepared by thoroughly mixing component 7 and component 2, followed by addition of component 9 during stirring.

Mixture 2: Another mixture is prepared by admixing component 8, component 3 and component 4, 5 and 6 in component 1.

Mixture 1 is added to mixture 2 during stirring to obtain a lotion according to the present invention.

Test Results of the Composition of Example 3

In a test period of 90 days, 87 women of age 21 to 72 years (average 49 years) were two times per day (morning and evening) administered 1 tablet of example 3.

Subsequently the test subjects were filling in a questionnaire wherein each subject was requested to state whether or not she agreed to the statements set out.

The table 3 below indicates the number and percentages of the subjects confirming the statements referred.

TABLE 3

| Statement referred | Number of subjects confirming the statement | Percentage of subjects confirming the statement (%) |
| --- | --- | --- |
| I am more satisfied with my skin | 40 | 46 |
| My skin feels more moisturised than before | 48 | 55 |
| My skin feels more elastic than before. | 29 | 33 |
| My skin feels much more fresh than before | 48 | 55 |
| I find the skin of my body more beautiful than before | 23 | 26 |
| I experience less dryness on my legs | 37 | 42 |

Table 3 shows that the administration of the composition has a useful effect on the skin of the subjects.

In addition to the subjective test above, an objective test was also carried out on the test subject mentioned above.

A number of objective parameters of the forearm skin were measured before and after a three months period with a daily intake of two tablets according to example 3.

The parameters were measured using the following instruments:
1. Dermascan C—Ultrasound Scanner
2. DermaLab, Suction Cup/Elasticity module
3. DermaLAB, Electrical Impedance/Water Content module
4. DermaLab, Trans Epidermal Water Loss/TEWL module
5. DermaSpectrometer, Erythema (Redness)

which are all available from Cortex International ApS, Hadsund, Denmark.

The Ultrasound images by Dermascan were evaluated by an automated computer analysis including edge detection. The structural density of the entire skin cross section was measured as average and as the percentage of strongly organized (i.e. young) areas within the cross section plus the percentage of weakly organized (old/damaged/edema) areas within the cross section.

The DermaLab elasticity module was used to measure the elasticity module/the stiffness of the skin.

The DermaLab moisture module was used to measure the moisturization of the epidermal structure.

The DermaLab TEWL module was used to measure the integrity of the skin's barrier function.

The DermaSpectrometer was used to measure the skin's degree of irritation

Table 4 below sets out the results obtained.

TABLE 4

| Type of measurement | Objective results (averaged) |
| --- | --- |
| Ultrasound | The collagen fibres became 25% more dense<br>Skin area with damage and oedema was reduced by 32%<br>Skin areas with dense structure increased by 22% |
| Elasticity | The rigidity of the skin decreased by 7% (softer skin) |
| Moisture balance | The moisture level increased by 59% |
| Water loss | The skin water loss decreased by 17% (indicating a healthier skin in balance) |
| Redness/irritancy | Skin redness decreased by 10% (indicating a slowdown of the skin ageing and a decrease irritancy of the skin from outside) |

The results set out in table 4 indicate that the composition according to the present invention has a beneficial effect of the cosmetic appearance of the skin.

Test Results of the Composition of Example 4

50 test subjects (25 men and 25 women) of age 20-45 years all affected by alopecia areata or other alopecia are two times each day in a period of six months administered the composition of example 4. The lotion is applied and rubbed into the scalp and allowed to remain on the scalp.

For each subject the number of active hair follicles as well as the growth rate of the hair in five areas of 1 cm×1 cm on the scalp is counted by means of videotrichogram at the beginning and after the end of the six month test period.

The average of increase of the number of active hair follicles during the test period is 17%.

The average of the increase in growth rate of the hair during the test period is 11%.

The above result indicates that the composition according to the present invention has a beneficial effect on hair growth.

The invention claimed is:

1. A composition comprising a tablet for oral administration, wherein the tablet comprises:
   a solid extract of a deep sea fish comprising protein, the protein extract being in a percentage range of about 15-70 wt %; and
   an extract of rooibos in a range of about 5 to 40 mg;
   as active components thereof; and
   one or more fillers or ancillary agents conventionally used in the formulation of tableted pharmaceutical compositions.

2. The composition according to claim 1, wherein the tablet is intended for daily dosage for cosmetic treatment of the skin and further comprising suitable ancillary agents and fillers as well as coating agents.

3. The composition according to claim 1, wherein the amount of the deep sea fish extract in the tablet is about 100 to 1600 mg.

4. The composition according to claim 1, wherein the amount of deep sea fish extract in the tablet is about 400 to 900 mg.

5. The composition according to claim 1, wherein the amount of rooibos in the tablet is about 10 to 30 mg.

6. The composition according to claim 1, wherein the amount of rooibos in the tablet is about 15 to 25 mg.

7. The composition according to claim 6, wherein the amount of rooibos in the tablet is 18 to 23 mg.

8. The composition according to claim 1, the tablet further comprising bearberry in a range of about 5 to 40 mg.

9. The composition according to claim 8, wherein the amount of bearberry in the tablet is about 8 to 35 mg.

10. The composition according to claim 8, wherein the amount of bearberry in the tablet is about 10 to 25 mg.

11. The composition according to claim 8, wherein the amount of bearberry in the tablet is 12 to 20 mg.

12. The composition according to claim 8, wherein the amount of bearberry in the tablet is about 14 to 18 mg.

13. The composition according to claim 8, wherein the composition is compressed into tablets with a net weight of approximately 531 mg each.

14. The composition according to claim 8, the tablet further comprising ingredients selected from the group consisting of horsetail extract in a range of 20 to 140 mg and shellfish extract in an amount less than 500 mg.

15. The composition according to claim 1, the tablet further comprising horsetail extract in a range of about 20 to 140 mg.

16. The composition according to claim 1, the tablet further comprising horsetail extract in a range of about 40 to 120 mg.

17. The composition according to claim 1, the tablet further comprising horsetail extract in a range of about 60 to 100 mg.

18. The composition according to claim 1, the tablet further comprising horsetail extract in a range of 80 mg.

19. The composition according to claim 15, the tablet further comprising shellfish extract in an amount less than about 500 mg.

20. The composition according to claim 1, the tablet further comprising diacetyl boldine.

21. The composition according to claim 1, the tablet further comprising ingredients selected from the group consisting of vitamin A, vitamin C, zinc, D-alpha-tocopherol, betaine, diazolidinyl urea, citric acid, sodium ascorbyl phosphate, alpha-lipoic acid, methylsulfonyl methane, and combinations thereof.

22. The composition according to claim 19, the tablet further comprising ingredients selected from the group consisting of vitamin A, vitamin C, zinc, D-alpha-tocopherol, betaine, diazolidinyl urea, citric acid, sodium ascorbyl phosphate, alpha-lipoic acid, methylsulfonyl methane, and combinations thereof.

* * * * *